United States Patent [19]

Kahr et al.

[11] 4,061,677

[45] Dec. 6, 1977

[54] PARTIAL DEHYDRATION OF CYCLOHEXANONE OXIME

[75] Inventors: Kurt Kahr, Hambach; Hanns Pohl, Lambsheim; Güenther Rapp, Ludwigshafen; Peter Lauz, Annweiler, all of Germany

[73] Assignee: BASF Aktiengesellschaft, Ludwigshafen, Germany

[21] Appl. No.: 700,541

[22] Filed: June 28, 1976

Related U.S. Application Data

[63] Continuation of Ser. No. 276,814, July 31, 1972, abandoned.

[30] Foreign Application Priority Data

Aug. 4, 1971 Germany .............................. 2138930

[51] Int. Cl.$^2$ ........................................... C07C 131/04
[52] U.S. Cl. ................................................ 260/566 A
[58] Field of Search ..................................... 260/566 A

[56] References Cited

U.S. PATENT DOCUMENTS

| 2,820,825 | 1/1958 | Hillyer et al. | 260/566 A |
| 3,002,996 | 10/1961 | Meier et al. | 260/566 A |

*Primary Examiner*—Gerald A. Schwartz
*Attorney, Agent, or Firm*—Keil, Thompson & Shurtleff

[57] ABSTRACT

The application relates to a process for partial dehydration of cyclohexanone oxime by treatment with an aqueous solution of an inorganic salt, the crude cyclohexanone oxime being extracted at above its melting point countercurrently in an extraction column with a concentrated solution of ammonium or/and hydroxylammonium salt. The salt solution may be used again after concentration. This may be effected by simple evaporation.

6 Claims, 1 Drawing Figure

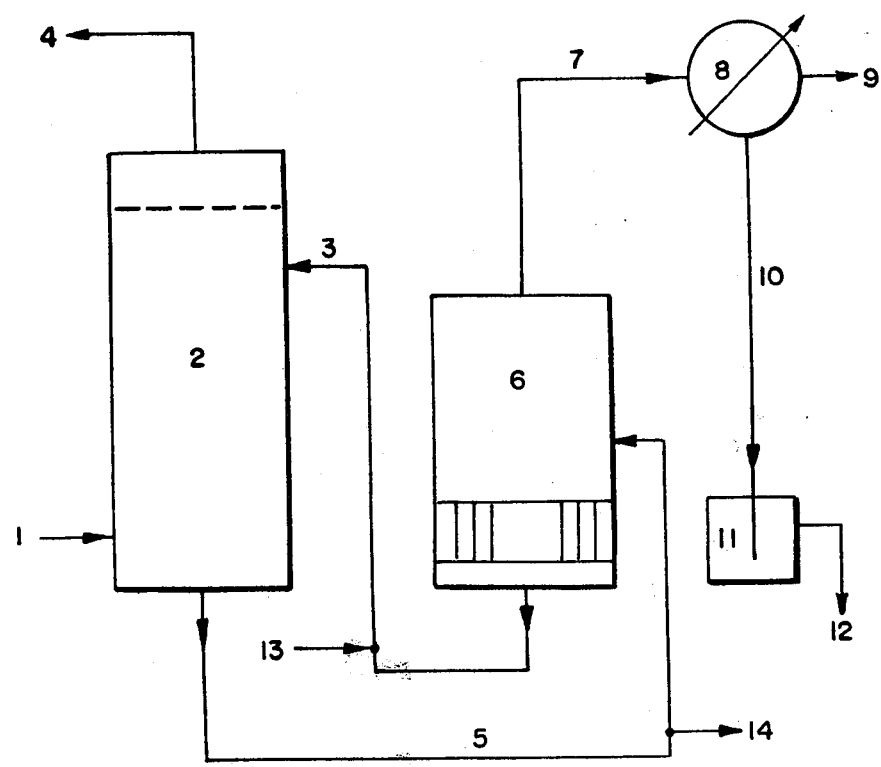

PARTIAL DEHYDRATION OF CYCLOHEXANONE OXIME

This is a continuation, of application Ser. No. 276,814 filed July 31, 1972, now abandoned.

It is known that cyclohexanone oxime may be prepared by oximation of cyclohexanone with a hydroxylammonium salt solution while neutralizing the acid formed by means of ammonia or another base. The cyclohexanone oxime thus obtained contains water. The water content of the cyclohexanone oxime separated from this two-phase mixture depends on the concentration of the resultant salt in the separated aqueous phase and on the temperature. Some of the water can be withdrawn from the oxime and the water content of the oxime thus decreased by extracting the oxime with a more concentrated salt solution than the separated salt solution. As a result of this partial withdrawal of water the oxime becomes far better suited for further processing by rearrangement with a strong anhydrous mineral acid such as oleum to form caprolactam.

While in conventional oximation of cyclohexanone with a solution of hydroxylammonium sulfate according to the Raschig method a cyclohexanone oxime having from 4 to 5% of moisture is obtained, oximation with a hydroxylammonium sulfate solution which has been obtained by catalytic reduction of nitric oxide with hydrogen in the presence of dilute sulfuric acid and which contains less ammonium sulfate gives an oxime having a moisture content of about 7%.

We have now found that the partial dehydration of crude cyclohexanone oxime with an aqueous solution of an inorganic salt can be carried out continuously in a simple manner by extracting crude cyclohexanone oxime heated above its melting point countercurrently in an extraction column with a concentrated solution of ammonium salt and/or hydroxylammonium salt, then separating the salt solution from the partly dehydrated cyclohexanone oxime, concentrating it again by evaporation and returning it for dehydration of the oxime.

It is found surprisingly that no enrichment of the impurities in the aqueous solution which is recycled takes place, but even a further purification of the oxime occurs. The residual cyclohexanone is either separated or completely reacted and also other impurities which are volatile in steam are removed.

Particularly suitable ammonium salt solutions are concentrated ammonium sulfate and/or hydroxylammonium sulfate solutions. Solutions of ammonium salts of other mineral acids, as for example phosphate or chloride solutions, can also be used. The concentrated hydroxylammonium salt solutions which at the temperature of the molten oxime are almost saturated solutions have the advantage that they not only exhibit an extractive effect with respect to the water and extractable impurities in the oxime but also have an after-oximating action. Thus residues of cyclohexanone still contained in the cyclohexanone oxime and usually amounting to up to 0.1% by weight are completely removed by oximation. Mixtures, as for example ammonium or hydroxylammonium sulfate solutions, may be used for the partial dehydration of cyclohexanone oxime instead of pure ammonium or hydroxylammonium salts. To achieve the greatest possible degree of dehydration of the technical-grade cyclohexanone oxime, concentrated aqueous salt solutions are used which may be practically saturated. The extraction may however be carried out with less concentrated salt solutions so that in this way any desired moisture content of the cyclohexanone oxime up to a maximum content of 9% by weight of $H_2O$ may be set up.

The partial dehydration of the moist technical-grade cyclohexanone oxime should be carried out at a temperature above the melting point of the aqueous oxime, i.e. above 65° C and below the boiling point of the salt solution. It is preferred to maintain a temperature of from 75° to 95° C.

In general, a constant water content of from 4 to 6% is set up in the cyclohexanone oxime by the extraction and partial dehydration of the cyclohexanone oxime with the concentrated ammonium and/or hydroxylammonium salt solutions by appropriate choice of the type and concentration of the solutions. Thus for example an industrially produced cyclohexanone oxime having a water content of 7.2% is brought by extraction at 85° C with a 48% ammonium sulfate solution to a water content of 5.0% and with a 62% hydroxylammonium sulfate solution to a water content of 4.2%.

The pH of the salt solution used for extraction of the cyclohexanone oxime should preferably be adjusted to a neutral or weakly acid reaction. When using an ammonium salt solution the pH may be for example at about 5 and in the case of a hydroxylammonium salt solution at about 3.

The partial dehydration of the oxime is advantageously carried out in a heated tower or a column having for example sieve plates or rotating discs by a countercurrent method, separation of the layers being carried out in the upper section of the column. The partly dehydrated oxime may be withdrawn from the upper section of the column through an overflow, while the only slightly diluted salt solution is drained away at the bottom and recycled to the evaporation unit. The relative proportions of recycled salt soluton and cyclohexanone oxime feed for the extractive dehydration may vary within wide limits. Normally more than 0.3 part by volume of concentrated salt solution to 1 part by volume of cyclohexanone oxime is adequate. Evaporation of the salt solution may be carried out in an evaporator in which the water taken up from the oxime and the impurities which are volatile in steam are distilled off so that the solution is recovered in the same concentration of salt and can be used again for dehydration of oxime. Concentration of the salt solution is advantageously carried out at slightly subatmospheric pressure. It is however also possible to use atmospheric or moderately superatmospheric pressure. It is advantageous to control the pressure so that the evaporation temperature is about the same as the temperature used in the extractive dehydration of the oxime.

To replenish or exchange the recycling concentrated salt solution, fresh ammonium and/or hydroxylammonium salt solution may be supplied to the circulation system and an equivalent amount of the used solution withdrawn. Amounts of only up to 3% of a fresh salt solution is adequate based on the oxime used. Ammonium sulfate solution occurring in the oximation may for example be used for this purpose.

The accompanying drawing shows a diagram for a plant in which the process according to this invention may be carried out.

Molten cyclohexanone oxime containing water flows through line 1 into an extraction column 2 and rises through the salt solution. The parting plane between salt solution and oxime forms in the upper portion of the column. Concentrated salt solution is supplied to the extraction column 2 through line 3. Partly dehydrated oxime is drawn off at the top of the column 2 through line 4. At the lower part of the column the slightly diluted salt solution passes through line 5 into a distillation column 6 in which the water taken up by the oxime is evaporated again and the original salt concentration is restored. The vapors escape through line 7 and are condensed in condenser 8, a vacuum being produced through line 9. The condensate flows through line 10, receiver 11 and leaves through line 12. The concentrated salt solution leaves column 6 in the lower portion and flows through line 3 back into the extraction column. Fresh salt solution and spent salt solution may be supplied and withdrawn through lines 13 and 14.

The following Examples illustrate the invention.

EXAMPLE 1

126 parts by volume of molten industrial cyclohexanone oxime having a water content of 7% is extracted at 80° C in a plant as shown in the drawing described above in an extraction column fitted with sieve plates with 30 parts by volume of a concentrated solution of ammonium-hydroxylammonium sulfate which contains 47% by weight of ammonium sulfate and 10% by weight of hydroxylammonium sulfate at a pH of 4.9 and 80° C. 123 parts by volume of cyclohexanone oxime having a content of 4.8% of water and 0.05% of cyclohexanone is obtained at the top of the extraction column. 2.9 parts by volume of water is distilled off from the recycle sulfate solution in the distillation column at 80° C and a vacuum of 280 mm Hg.

EXAMPLE 2

125 parts by volume of cyclohexanone oxime having 7.2% of moisture is extracted at 85° C in the same apparatus as in Example 1 with 50 parts by volume of a concentrated 62% by weight hydroxylammonium sulfate solution at a pH of 3.0. After the extraction 122 parts by volume of cyclohexanone oxime is obtained with 4.2% of moisture and without any trace of cyclohexanone. 3.9 parts by volume of water is distilled off from the recycled hydroxylammonium sulfate solution in the distillation column at 85° C and a vacuum of 340 torr.

EXAMPLE 3

In the same apparatus as in Example 1, 111 parts by volume of cylcohexanone oxime having a water content of 7.0% is extracted countercurrently at 85° C with 18 parts by volume of a 47% by weight ammonium sulfate solution. The pH of the recycled ammonium sulfate solution is 5.4. The water content of the cyclohexanone oxime obtained is 5.0%. The content of impurities in the oxime detected by gas chromotography has been reduced from 1690 to 850 ppm. 1.92 parts by volume of water is distilled off from the recycle ammonium sulfate solution.

We claim:

1. A process for partial dehydration of cyclohexanone oxime by treatment with an aqueous solution of an inorganic salt wherein crude cyclohexanone oxime is extrated countercurrently at a temperature of from 65° C to the boiling temperature of the two-phase mixture in an extraction column with a concentrated solution of a salt selected from the group consisting of ammonium sulfate, hydroxylammonium sulfate, ammonium chloride, ammonium phosphate, and mixtures of ammonium sulfate and hydroxylammonium sulfate, and the salt solution is separated from the partly dehydrated cyclohexanone oxime, concentrated again by evaporation and returned for dehydration of the oxime.

2. A process as claimed in claim 1 wherein a concentrated ammonium sulfate solution is used for dehydration.

3. A process as claimed in claim 1 wherein a concentrated hydroxylammonium sulfate solution is used for dehydration.

4. A process as claimed in claim 1 wherein the extractive dehydration is carried out at a pH of from 3 to 6.

5. A process as claimed in claim 1 wherein concentration of the recycled salt solution is carried out in a vacuum.

6. A process as claimed in claim 1 wherein the extraction dehydration temperature is from 75° to 95° C.

* * * * *